(12) United States Patent
Chang

(10) Patent No.: US 12,169,170 B2
(45) Date of Patent: Dec. 17, 2024

(54) SENSING PACKAGE, OPTICAL MODULE AND METHOD FOR DETECTING LIGHT

(71) Applicant: Advanced Semiconductor Engineering, Inc., Kaohsiung (TW)

(72) Inventor: Wei-Hao Chang, Kaohsiung (TW)

(73) Assignee: ADVANCED SEMICONDUCTOR ENGINEERING, INC., Kaohsiung (TW)

(*) Notice: Subject to any disclaimer, the term of this patent is extended or adjusted under 35 U.S.C. 154(b) by 318 days.

(21) Appl. No.: 17/730,123

(22) Filed: Apr. 26, 2022

(65) Prior Publication Data

US 2023/0341317 A1    Oct. 26, 2023

(51) Int. Cl.
*G01N 21/17* (2006.01)
*G06F 3/01* (2006.01)

(52) U.S. Cl.
CPC . *G01N 21/1717* (2013.01); *G01N 2021/1725* (2013.01); *G01N 2201/0636* (2013.01); *G06F 3/011* (2013.01)

(58) Field of Classification Search
CPC ....... G01N 21/1717; G01N 2021/1725; G01N 2201/0636; G01N 2021/0106; G01N 2021/1738; G01N 21/01; G06F 3/011; G06F 3/015; A61B 5/0059; A61B 5/02427; A61B 5/14552; A61B 5/6824; A61B 2562/0233; A61B 2562/164
USPC ........ 356/136, 614, 610, 437, 436, 445, 338
See application file for complete search history.

(56) References Cited

U.S. PATENT DOCUMENTS

| | | | |
|---|---|---|---|
| 2013/0086977 A1* | 4/2013 | Wong | G01J 5/045 73/31.05 |
| 2014/0226149 A1* | 8/2014 | Coates | G01N 21/31 356/51 |
| 2016/0231244 A1* | 8/2016 | Camargo | H01L 31/0304 |
| 2020/0103334 A1* | 4/2020 | Santangelo | G02B 19/0023 |
| 2020/0103339 A1* | 4/2020 | Castagna | G01N 21/3504 |

* cited by examiner

*Primary Examiner* — Isiaka O Akanbi
(74) *Attorney, Agent, or Firm* — FOLEY & LARDNER LLP

(57) ABSTRACT

The present disclosure provides a sensing package. The sensing package includes a carrier configured to face an object to be inspected and an emitter disposed adjacent to the carrier. The emitter is configured to emit a first light propagating in a first direction. The sensing package further includes a component configured to change the first light into a second light propagating in a second direction different from the first direction. An optical module and a method for detecting light are also provided.

8 Claims, 14 Drawing Sheets

SENSING PACKAGE, OPTICAL MODULE AND METHOD FOR DETECTING LIGHT

BACKGROUND

1. Technical Field

The present disclosure relates to a sensing package, an optical module and a method for detecting light.

2. Description of the Related Art

Numerous methods have been developed to obtain information or signals reflecting physical activity and/or health through non-invasive subject measurements. For example, light emitters and light receivers may be integrated into wearable devices. To enhance comfort of the wearable devices and meet market needs, it is desired to reduce the thickness of the wearable devices.

SUMMARY

In some arrangements, a sensing package includes a carrier configured to face an object to be inspected and an emitter disposed adjacent to the carrier. The emitter is configured to emit a first light propagating in a first direction. The sensing package further includes a component configured to change the first light into a second light propagating in a second direction different from the first direction.

In some arrangements, an optical module includes a carrier configured to face an object to be inspected and an emitter device disposed adjacent to the carrier. The emitter device is configured to emit a first light. The optical module further includes a receiver device disposed between the carrier and the object. The optical module further includes an optical device configured to direct the first light toward the object. The receiver device is configured to receive a second light reflected by the object.

In some arrangements, a method for detecting light includes emitting a first light propagating in a first direction not directed toward an object to be inspected and changing the first light into a second light propagating in a second direction toward the object. The method also includes receiving a third light reflected by the object and propagating in a third direction.

BRIEF DESCRIPTION OF THE DRAWINGS

Aspects of some arrangements of the present disclosure are best understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1A:
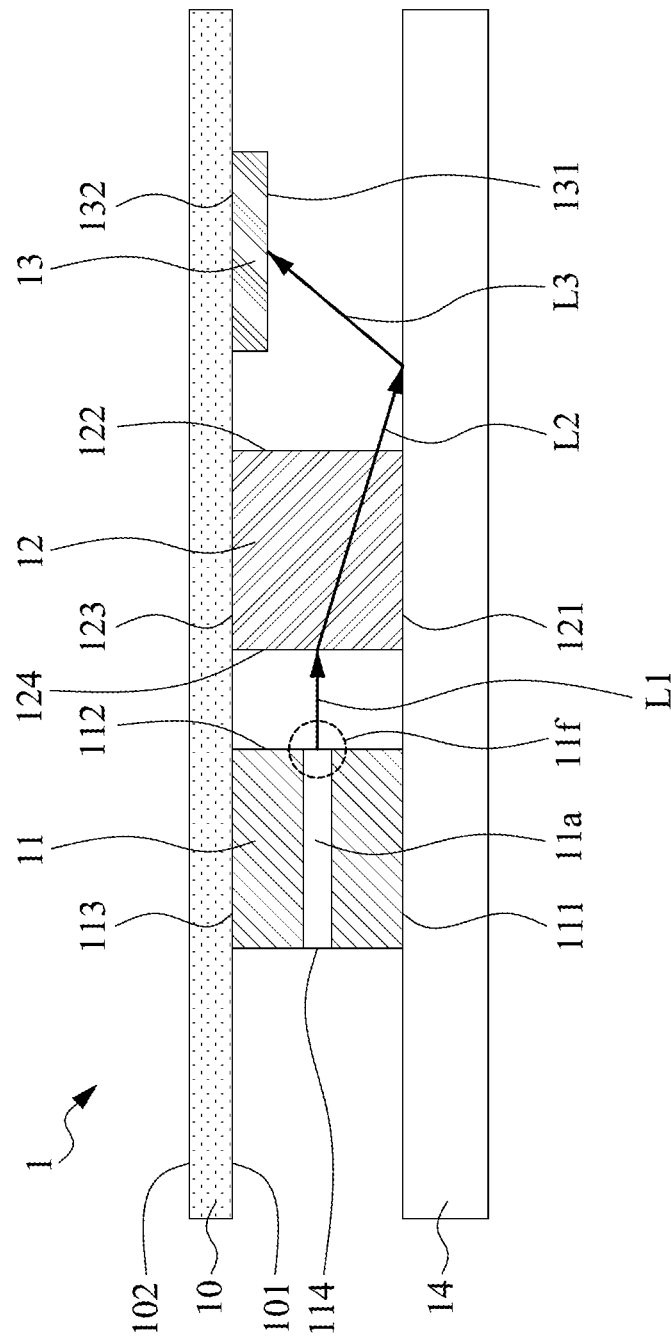
FIG. 1A is a cross-section of a sensing package and an object to be inspected in accordance with some arrangements of the present disclosure.

The following disclosure provides for many different arrangements, or examples, for implementing different features of the provided subject matter. Specific examples of components and arrangements are described as follows to explain certain aspects of the present disclosure. These are, of course, merely examples and are not intended to be limiting. For example, the formation of a first feature over or on a second feature in the description that follows may include arrangements in which the first and second features are formed or disposed in direct contact, and may also include arrangements in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various arrangements and/or configurations discussed.

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of arrangements of this disclosure are not deviated from by such arrangement.

The following description involves a sensing package and a method for detecting light. FIG. 1A is a cross-section of a sensing package 1 and an object 14 to be inspected (hereinafter object 14) in accordance with some arrangements of the present disclosure.

In some arrangements, the sensing package 1 may include or be a part of an electronic component or an electronic module, such as a system-in-package (SiP) module. In some arrangements, the sensing package 1 may include a wearable device, such as a smartwatch, a smart band, or another smart wearable device.

In some arrangements, the sensing package 1 may be a piece of equipment that detects an external signal using various detection devices (such as receivers or sensors). In some arrangements, the sensing package 1 may execute data communication with a base station or a terminal device (such as a mobile phone) in a wireless communications manner, such as via radio frequency identification technology or short-range wireless communications technology. In some arrangements, the sensing package 1 may be used in combination with an electronic device (such as a signal processing device) and/or other corresponding external devices for further processing acquired signals.

For ease of description, a smartwatch is used purely as an example for specific descriptions in specific arrangements of the present invention. Configuration or application of the sensing package 1 is for illustrative purposes only, and not intended to limit the present disclosure.

Referring to FIG. 1A, the sensing package 1 may include a carrier 10, an emitter 11, a component 12 and a receiver 13. The sensing package 1 may be adjacent to the object 14.

In some arrangements, the carrier 10 may include a substrate. For example, the carrier 10 may include, a printed circuit board, such as a paper-based copper foil laminate, a composite copper foil laminate, or a polymer-impregnated glass-fiber-based copper foil laminate. In some arrangements, the carrier 10 may include an interconnection structure, such as a redistribution layer (RDL) or a grounding element.

The carrier 10 may include a surface 101 and a surface 102 opposite to the surface 101. In some arrangements, the surface 101 may be configured to face the object 14. For example, when the sensing package 1 is worn by a user, the surface 101 may face the user's skin.

The carrier 10 may include one or more conductive pads (not shown) in proximity to, adjacent to, or embedded in and exposed by the surface 101 and/or 102 of the carrier 10. The carrier 10 may include a solder resist (not shown) on the surface 101 and/or 102 of the carrier 10 to expose at least a portion of the conductive pads for electrical connections.

The emitter 11, the component 12, and the receiver 13 may be disposed on the surface 101 of the carrier 10. The component 12 may be disposed between the emitter 11 and the receiver 13. In some arrangements, the emitter 11 and the receiver 13 may each be electrically connected to one or more other devices and to the carrier 10 (e.g., to the RDL), and electrical connection may be attained by way of flip-chip or wire-bond techniques.

In some arrangements, the component 12 may not be electrically connected to one or more other devices or to the carrier 10. For example, the component 12 may be operated without electrical power. However, in some other arrangements, the component 12 may also be electrically connected to one or more other devices and to the carrier 10.

In some arrangements, an encapsulant (such as the encapsulant 16 in FIG. 1B) may be disposed on the surface 101 of the carrier 10 to cover or encapsulate the emitter 11, the component 12 and the receiver 13. However, in some other arrangements, the encapsulant may be omitted and the emitter 11, the component 12 and the receiver 13 may each be at least partially exposed to air.

In some arrangements, the carrier 10 and the encapsulant may each be soft and flexible enough for a user of the sensing package 1 to wear comfortably for an extended time period. In some arrangements, the carrier 10 and the encapsulant may each be relatively more resistant to stress, impact, twisting, or other physical or structural changes. In some arrangements, the carrier 10 and the encapsulant may each be conformal to the contour or the shape of a portion of the object 14.

In some arrangements, the emitter 11, the component 12 and the receiver 13 may be disposed between the carrier 10 and the object 14. In some arrangements, a surface of the emitter 11 and a surface of the component 12 may be substantially at the same elevation relative to the surface 101, along a vertical axis perpendicular to or traversing the surface 101 or 102. In some arrangements, the emitter 11 and the component 12 may contact the object 14. For example, the emitter 11 and the component 12 may each have a surface (e.g., the surfaces 113 and 123) facing or contacting the carrier 10 and an opposite surface (e.g., the surfaces 111 and 121) facing or contacting the object 14. For example, the emitter 11 and the component 12 may have the same thickness. In some arrangements, the thickness of the emitter 11 and the thickness of the component 12 may be the shortest distance between the carrier 10 and the object 14.

However, in some other arrangements, a surface of the emitter 11 and a surface of the component 12 may not be at the same elevation relative to the surface 101, along a vertical axis perpendicular to or traversing the surface 101 or 102. For example, the emitter 11 and the component 12 may have different thicknesses. For example, the emitter 11 may contact the object 14 while the component 12 may not, and vice versa.

In some arrangements, a surface (e.g., the surface 131) of the receiver 13 facing the object 14 may be spaced apart from the object 14. For example, the object 14 may be supported by the emitter 11 and the component 12. Therefore, the receiver 13 may not contact (or be physically separated from) the object 14.

The emitter 11 (or an emitter device) may include a light source or any suitable device configured to generate or emit light "L1." The light may include one or more light beams. The light may include a set of lights or a group of lights. The light may be visible light, such as laser light. As used herein, the term "light beam" may refer to a beam of light energy that radiated from a light source (e.g., the emitter 11) in a direction. The light beams may be visible light beams, such as laser beams. For example, the light L1 (which may include laser light) from the emitter 11 may be monochromatic, directional, and coherent. For example, the light L1 from the emitter 11 may be of a single wavelength or frequency. For example, the light L1 from the emitter 11 may be non-divergent or have relatively low divergence. For example, the light L1 from the emitter 11 may be parallel lights propagating in a single direction. For example, the light L1 from the emitter 11 may be in phase. In some arrangements, the light L1 from the emitter 11 may be in the form of continuous waves or light pulses.

However, in some other arrangements, the light may include other electromagnetic waves, such as radio waves, microwaves, and x rays.

The emitter 11 may include a laser configured to generate or emit one or more laser beams. For example, the emitter 11 may include a laser diode, such as an edge-emitting laser (also called an in-plane laser), a vertical-cavity surface-emitting laser, or other single frequency laser diodes. For example, the emitter 11 may include an active layer 11*a* for generating one or more laser beams and cladding layers on opposite sides of the active layer 11*a*. Contacts or electrodes (e.g., the anode and cathode) may be on the surfaces 111 and 113. As shown, the surface 111 may face or contact the object 14 and the surface 113 may face or contact the carrier 10.

The laser beams may radiate from an end facet 11*f* (or front facet, or a light-emitting surface or region) on the surface 112 of the emitter 11. The emitter 11 may be configured to emit the light L1 toward the component 12, and the surface 112 of the emitter 11 may face the component 12.

In some arrangements, the surface 112 of the emitter 11 may not face the object 14. In some arrangements, the light L1 from the emitter 11 may not directly propagate toward the object 14. For example, the propagating direction of the light L1 may not be directed toward the object 14. For example, the propagating direction of the light L1 may not intersect with the object 14. For example, the object 14 may not be directly exposed to the light L1 from the emitter 11. For example, the object 14 may be indirectly exposed to the light L1 from the emitter 11. For example, one or more optical devices or optics (such as the component 12) may be located downstream of the emitter 11 for controlling, affecting, or treating the light L1 from the emitter 11.

In some arrangements, such optics may include transmissive elements and/or reflective elements, such as optical prisms, lenses, optical waveguides, reflecting surfaces (e.g., mirrors), etc. The optics may control optical parameters of the light L1, such as the direction, propagation property or shape (e.g., convergent, divergent, collimated), spot size, angular distribution, temporal and spatial coherence, intensity profile, etc.

For example, the component 12 may be configured to change the propagating direction of the light L1. For example, the component 12 may be configured to change the light L1 into light L2 having a propagating direction different from that of the light L1. For example, the component 12 may be configured to direct the light L1 toward the object 14. In some arrangements, the propagating direction of the light L1 may be changed one time and become the light L2 as shown in FIG. 1A. However, in some other arrangements, the propagating directions from the light L1 to the light L2 may change more than one time, and there may be light having more than two different propagating directions in the component 12.

As mentioned, the component 12 may have a surface 121 facing or contacting the object 14 and the surface 123 facing or contacting the carrier 10. The component 12 may have a surface 124 (extending between the surface 121 and the surface 123) configured to receive the light L1 and a surface 122 (extending between the surface 121 and the surface 123) configured to output the light L2. The surface 124 and the surface 122 may be different, such as opposite to each other. The surface 124 may face the emitter 11 and the surface 122 may face the receiver 13.

Figure 1B:
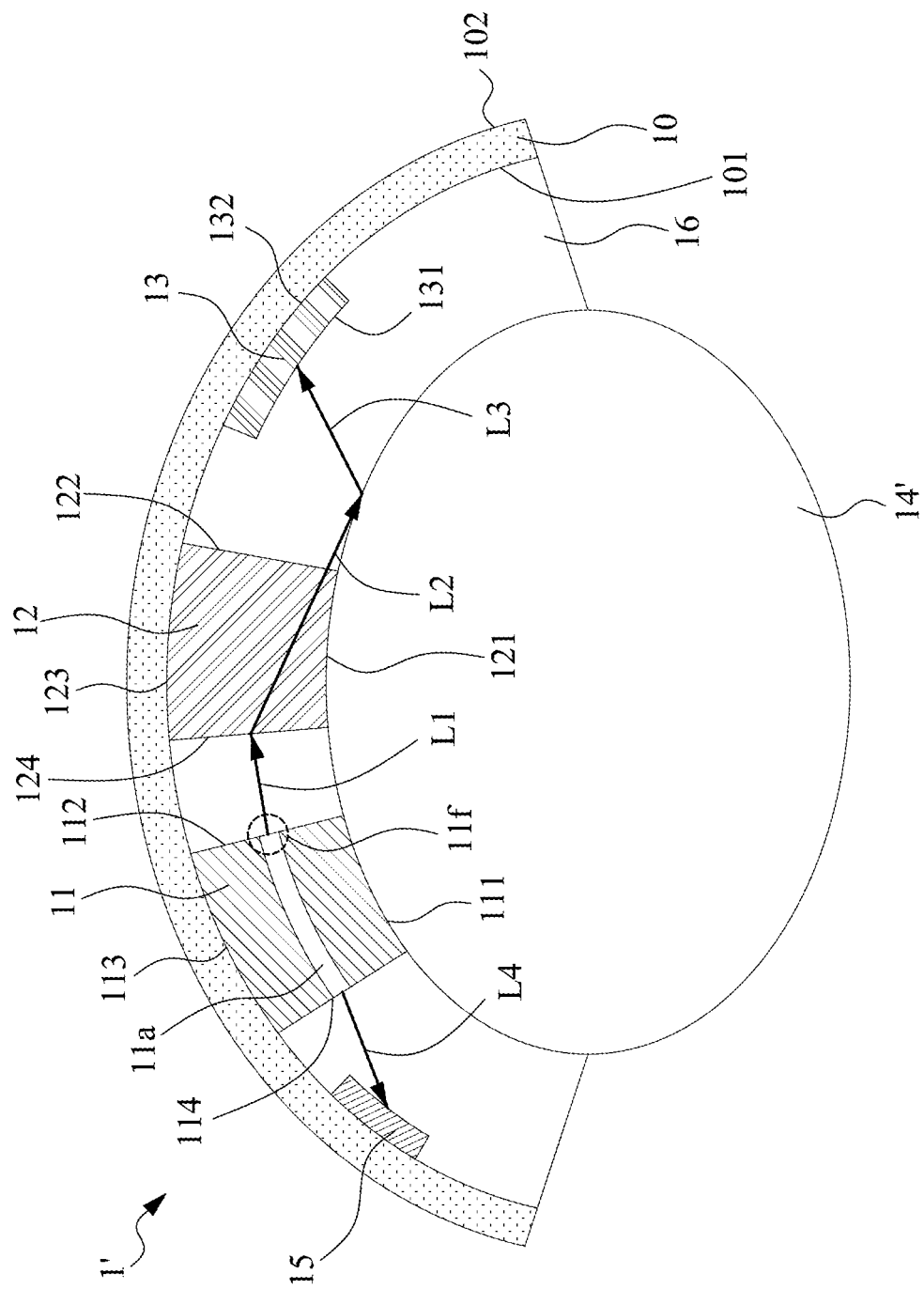
FIG. 1B is a cross-section of a sensing package and an object to be inspected in accordance with some arrangements of the present disclosure.

In some arrangements, the component 12 may include transmissive elements through which the light L1 may pass and change direction therein. For example, the light L2 may propagate in the component 12. For example, the light L1 and the light L2 may propagate in different media, possibly of different refractive indices. The light L1 may propagate in air as shown in FIG. 1A or n the encapsulant 16 as shown in FIG. 1B.

In some arrangements, the light L2 from the component 12 may directly propagate toward the object 14. For example, the propagating direction of the light L2 may be directed toward the object 14. For example, the object 14 may be directly exposed to the light L2 from the component 12.

The light L2 may be reflected by the object 14 as light L3. For example, the light L3 may be reflections of the light L2 reflected by the object 14. In some arrangements, the light L1, the light L2 and the light L3 may have different propagating directions.

The receiver 13 (or a receiver device) may be configured to receive the light L3. The receiver 13 may include an optical sensor, such as a photodiode (PD). The receiver 13 may have an active surface (e.g., the surface 131) facing the object 14 and a backside surface or rear surface (e.g., the surface 132) opposite to the active surface. The active surface (e.g., the surface 131) may be spaced apart from the object 14 and configured to receive the light L3.

The receiver 13 may be configured to convert light into an electronic signal. For example, when the sensing package 1 is worn by a user, the receiver 13 may be configured to detect or collect one or more signals (e.g., biosignals) or pieces of information associated with the user.

For example, the light L1 propagating in a direction from the emitter 11 may be changed by the component 12 into light L2 propagating in another direction. The light L2 from the component 12 may reach the user's skin and be reflected (e.g., by skin or by hemoglobin in a blood vessel). The receiver 13 may receive the reflected light (e.g., the light L3) as an external signal.

In some arrangements, the sensing package 1 may further include an electronic device (such as a signal processing device) to further process (e.g., analysis, modify, synthesize, convert to a digital signal, and amplify, etc.) the external signal, so as to obtain the detection result, such as oxygen saturation (SpO2), heart rate (HR), heart rate variability (HRV), respiratory rate (breaths per minute, brpm), pulse travel time (PTT), electroencephalogram (EEG), electrocardiogram (ECG), electromyogram (EMG), electrooculogram (EOG), galvanic skin response (GSR), sweat composition, or other biologically-relevant information. In some other arrangements, the signal processing device may not be integrated within the sensing package 1.

The positions, functions, and number of components (or devices) in the sensing package 1 are not intended to limit the present disclosure. For example, there may be any number of components in the sensing package 1 due to design requirements. For example, the sensing package 1 may further include an electronic device to store and/or to transmit the external signal and/or the detection result. For example, the sensing package 1 may further include one or more optical components for guiding or directing the light L1 toward the object 14.

In FIG. 1A, the propagating directions from the light L1 to the light L3 change two times. There may be three different propagating directions. In some other arrangements, the propagating directions from the light L1 to the light L3 may change more than two times, and there may be more than three different propagating directions.

In a comparative arrangement, in order to reduce the thickness of the sensing package 1, the end facet 11*f* of the emitter 11 may be disposed proximal to the object 14 to reduce the light path of the light L1. However, a gap between the emitter 11 and the application end of the sensing package 1 that contacts the object 14 is needed for allowing the reflected light from the object 14 to propagate toward and be received by the receiver 13.

According to some arrangements of the present disclosure, using the optics (such as the component 12) to control, affect, or treat optical parameters (such as direction, propagation property or shape (e.g., convergent, divergent, collimated), spot size, angular distribution, temporal and spatial coherence, intensity profile, etc.) of the light L1, the end facet 11f of the emitter 11 may be positioned at any desired distance from the application end of the sensing package 1 that contacts the object 14. For example, the end facet 11f of the emitter 11 may face the component 12 and may not contact the object 14. The emitter 11 may be thinned from the cladding layers. Therefore, the thickness of the sensing package 1 can be further reduced. The flexibility of the sensing package 1 can be increased, and the user's experience can be enhanced.

FIG. 1B is a cross-section of a sensing package 1' and an object 14' in accordance with some arrangements of the present disclosure. The sensing package 1' and the object 14' are similar to the sensing package 1 and the object 14 in FIG. 1A except for the differences described as follows.

The object 14' may have a curved contour or shape. In some arrangements, the sensing package 1' may be conformal to the contour or the shape of a portion of the object 14' and may be curved. For example, when the sensing package 1' is worn on a wrist, the sensing package 1' may be conformal to the wrist and may be curved.

As shown in FIG. 1B, the emitter 11, the component 12 and the receiver 13 may each be conformal to the contour or the shape of a portion of the object 14' and have a curved surface.

In some arrangements, the light path of the light L1, the light path of the light L2, the light path of the light L3 and the light path of the light L4 may be affected by the curvature of the sensing package 1'. For example, the functionality (or the sensing function, or the sensing process) of the sensing package 1' may be affected by the curvature thereof.

For example, when the sensing package 1' is curved (or the curvature of the sensing package 1' is within a certain range), the propagating direction of the light L1 from the emitter 11 may be changed by the component 12 and the light L2 from the component 12 may reach the user's skin and may be reflected. The receiver 13 may receive the reflected light (e.g., the light L3) as an external signal.

If the sensing package 1' is not curved (or the curvature of the sensing package 1' is not within a certain range), the light path of the light L1, the light path of the light L2 and the light path of the light L3 may differ from those stated. For example, the light L1 may not propagate toward the component 12 or may not be received by (or incident on) the surface 124 of the component 12. For example, the light L2 may not propagate toward the object 14' or may not be reflected by the object 14'. For example, the light L3 may not propagate toward the receiver 13 or may not be received by the surface 131 of the receiver 13.

The sensing package 1' may further include a receiver 15 and an encapsulant 16. In some arrangements, the emitter 11 may be disposed between the receiver 15 and the receiver 13. In some arrangements, the emitter 11 may be configured to emit light L4 toward the receiver 15. The laser beams may radiate from a surface 114 of the emitter 11 facing the receiver 15.

The propagating direction of the light L4 may be opposite to the propagating direction of the light L1. In some arrangements, the intensity of the light L4 may be different from the intensity of the light L1. For example, the intensity of the light L4 may be less than the intensity of the light L1.

In some arrangements, the receiver 15 may be configured to receive the light L4. The receiver 15 may include an optical sensor, such as a photodiode (PD). The receiver 15 may be configured to convert light into an electronic signal. For example, when the sensing package 1' is worn by a user, the receiver 15 may be configured to monitor the stability of the emitter 11 based on, for example, the continuity, the time interval and/or the intensity of the light L4.

In some arrangements, the encapsulant 16 may include an epoxy resin having fillers, a molding compound (e.g., an epoxy molding compound or other molding compound), a polyimide, a phenolic compound or material, a material with a silicone dispersed therein, or a combination thereof. As mentioned, the encapsulant 16 may be soft and flexible enough for a user of the sensing package 1' to wear comfortably for an extended time period.

Figure 2A:
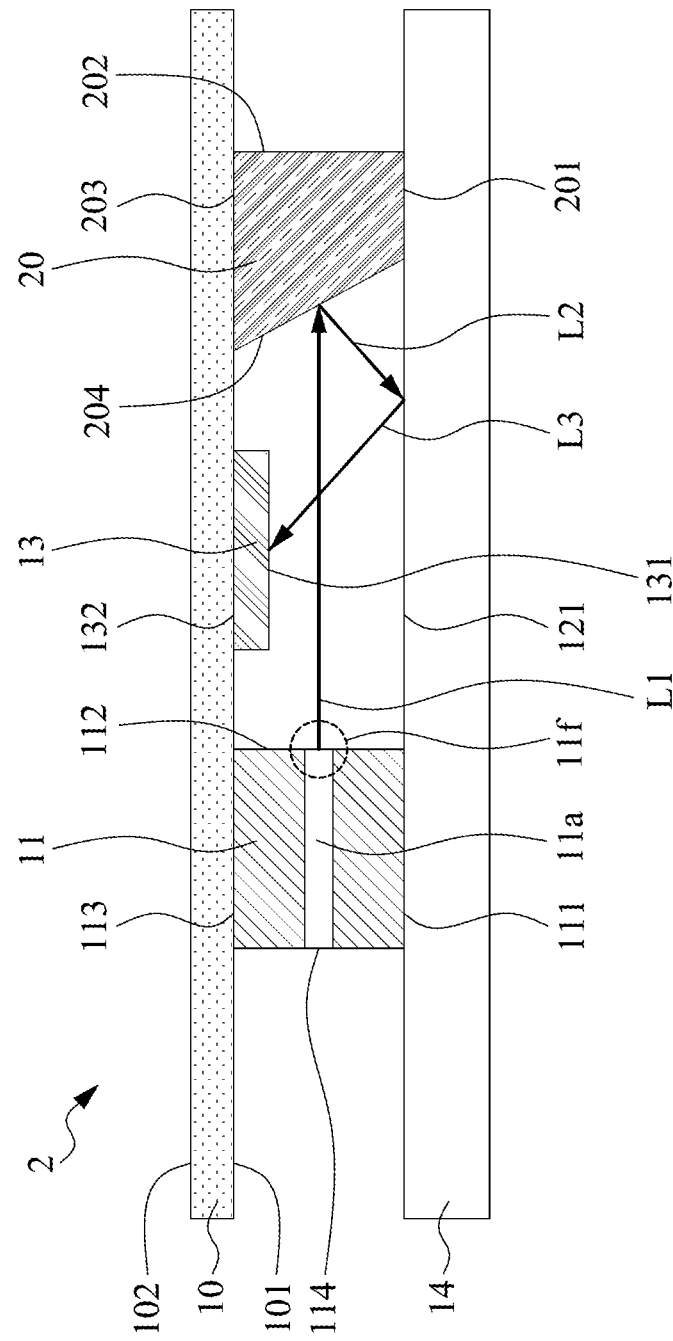
FIG. 2A is a cross-section of a sensing package and an object to be inspected in accordance with some arrangements of the present disclosure.

FIG. 2A is a cross-section of a sensing package 2 and the object 14 in accordance with some arrangements of the present disclosure. The sensing package 2 is similar to the sensing package 1 in FIG. 1A except for the differences described as follows.

The sensing package 2 may include a component 20. For example, the component 12 of the sensing package 1 may be replaced with the component 20 of the sensing package 2. The receiver 13 may be disposed between the emitter 11 and the component 20.

The component 20 may have a surface 201 facing or contacting the object 14 and the surface 203 facing or contacting the carrier 10. The component 20 may also have surfaces 202 and 204 extending between the surface 201 and the surface 203. The surface 204 may be configured to receive the light L1 and to output the light L2. In some arrangements, the surface 204 may face the emitter 11 and the receiver 13. In some arrangements, the surface 204 may be inclined with respect to the surface 101 of the carrier 10. For example, the surface 204 and the surface 101 may define an acute angle.

The surface 204 of the component 20 may be configured to change the propagating direction of the light L1. For example, the surface 204 of the component 20 may be configured to change the light L1 into light L2 having a propagating direction different from that of the light L1. For example, the surface 204 of the component 20 may be configured to direct the light L1 toward the object 14.

The surface 204 of the component 20 may be a reflecting surface (e.g., a mirror). For example, the light L1 may be reflected by the surface 204 of the component 20 as the light L2. For example, the light L2 may be reflections of the light L1 by the surface 204 of the component 20.

The light L1 and the light L2 may propagate in the same medium, such as media having the same refractive indices. The light L1 and the light L2 may propagate in air as shown in FIG. 2A or may propagate in the encapsulant 16 as shown in FIG. 2B.

The light L2 from the component 12 may directly propagate toward the object 14. For example, the propagating direction of the light L2 may be directed toward the object 14. For example, the object 14 may be directly exposed to the light L2 from the component 20. The light L2 may then be reflected by the object 14 as the light L3 and the receiver 13 may be configured to receive the light L3.

Figure 2B:
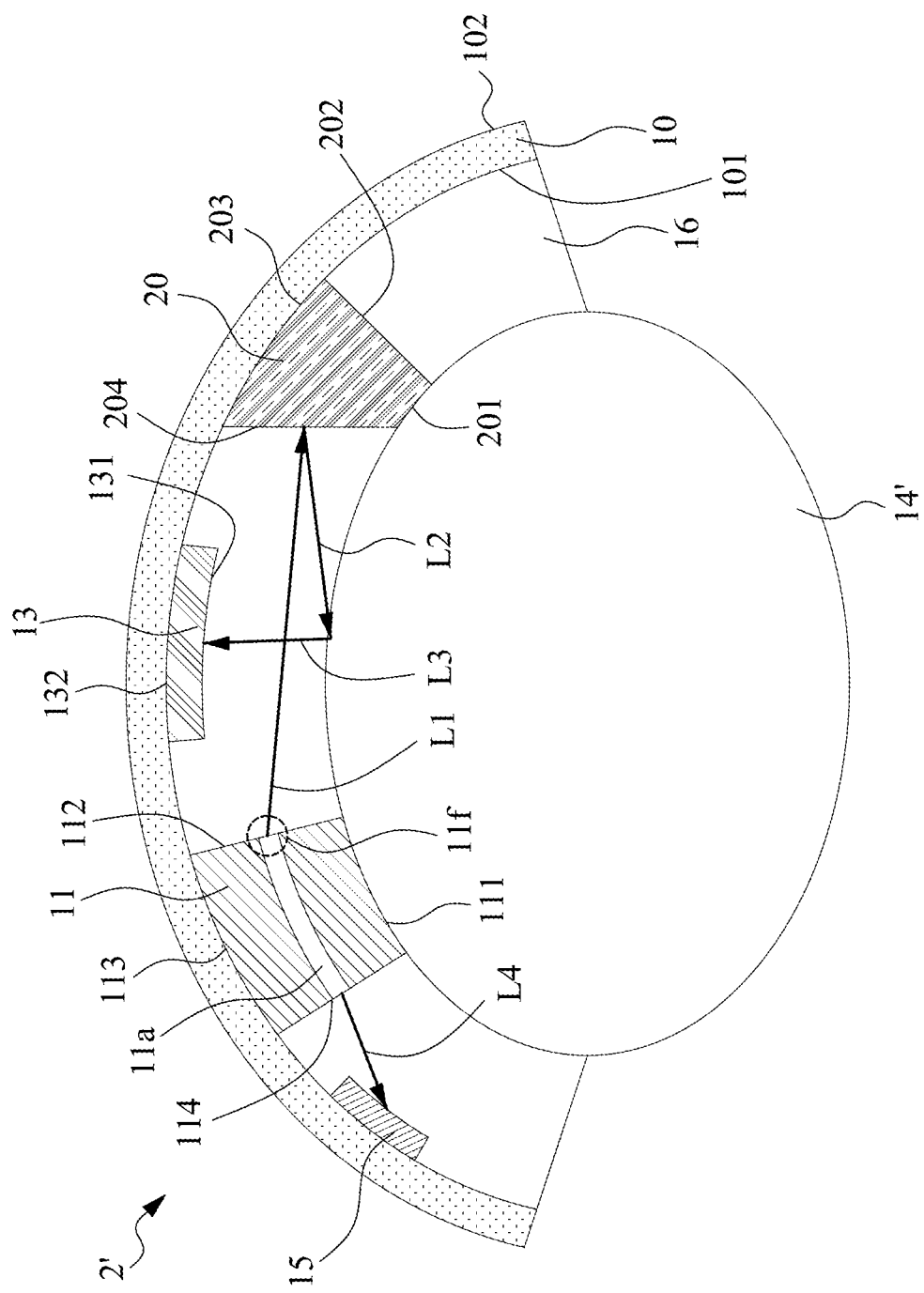
FIG. 2B is a cross-section of a sensing package and an object to be inspected in accordance with some arrangements of the present disclosure.

FIG. 2B is a cross-section of a sensing package 2' and the object 14' in accordance with some arrangements of the present disclosure. The sensing package 2' is similar to the sensing package 1' in FIG. 1B and the sensing package 2 in FIG. 2A except for the differences described as follows.

In some arrangements, the sensing package 2' may be conformal to the contour or the shape of a portion of the object 14' and may be curved. For example, when the sensing package 2' is worn on a wrist, the sensing package 2' may be conformal to the wrist and may be curved.

Similar to the sensing package 1' in FIG. 1B, the light path of the light L1, the light path of the light L2, the light path of the light L3 and the light path of the light L4 may be affected by the curvature of the sensing package 1'. For example, the functionality (or the sensing function, or the sensing process) of the sensing package 1' may be affected by the curvature thereof.

The sensing package 2' may further include the receiver 15 and the encapsulant 16, which are similar to the sensing package 1' in FIG. 1B.

Figure 3A:
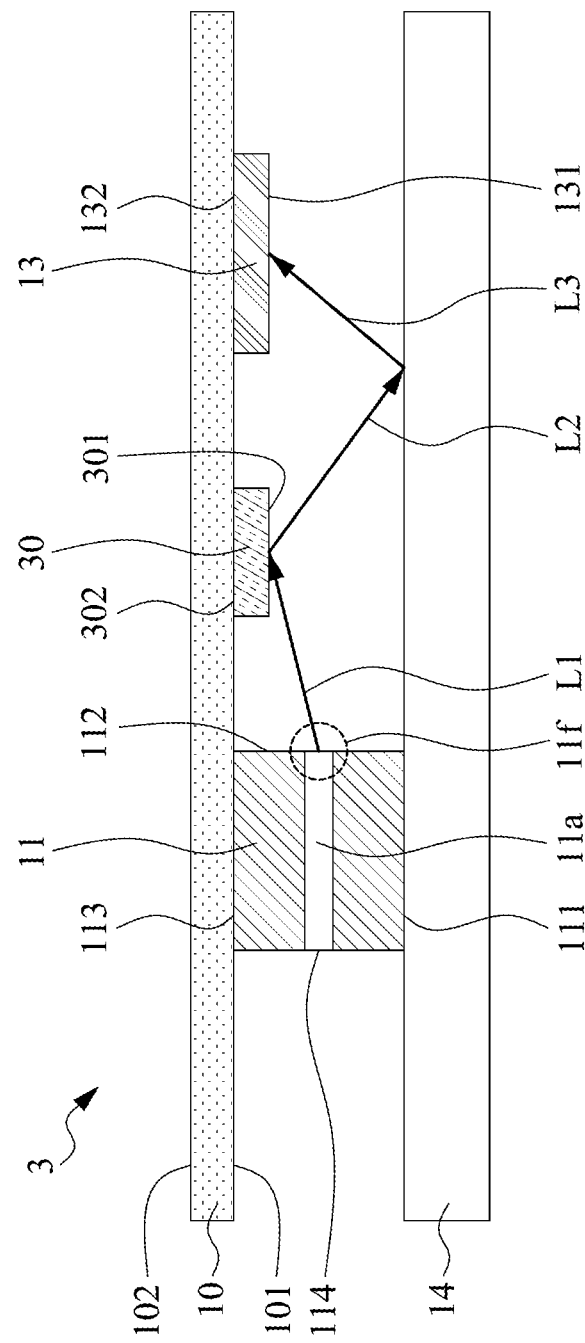
FIG. 3A is a cross-section of a sensing package and an object to be inspected in accordance with some arrangements of the present disclosure.

FIG. 3A is a cross-section of a sensing package 3 and the object 14 in accordance with some arrangements of the present disclosure. The sensing package 3 is similar to the sensing package 1 in FIG. 1A except for the differences described as follows.

The sensing package 3 may include a component 30. For example, the component 12 of the sensing package 1 may be replaced with the component 30 of the sensing package 3. The component 30 may be disposed between the emitter 11 and the receiver 13.

The component 30 may have a surface 301 facing the object 14 and the surface 302 facing or contacting the carrier 10. The surface 301 may be spaced apart from the object 14. The surface 301 may be configured to receive the light L1 and to output the light L2.

The surface 301 of the component 30 may be configured to change the propagating direction of the light L1. For example, the surface 301 of the component 30 may be configured to change the light L1 into light L2 having a propagating direction different from that of the light L1. For example, the surface 301 of the component 30 may be configured to direct the light L1 toward the object 14.

The surface 301 of the component 30 may be a reflecting surface (e.g., a mirror). For example, the light L1 may be reflected by the surface 301 of the component 30 as the light L2. For example, the light L2 may be reflections of the light L1 by the surface 301 of the component 30.

The light L1 and the light L2 may propagate in the same medium, such as media having the same refractive indices. The light L1 and the light L2 may propagate in air as shown in FIG. 3A or may propagate in the encapsulant 16 as shown in FIG. 3B.

The light L2 from the component 12 may directly propagate toward the object 14. For example, the propagating direction of the light L2 may be directed toward the object 14. For example, the object 14 may be directly exposed to the light L2 from the component 20. The light L2 may then be reflected by the object 14 as the light L3 and the receiver 13 may be configured to receive the light L3.

Figure 3B:
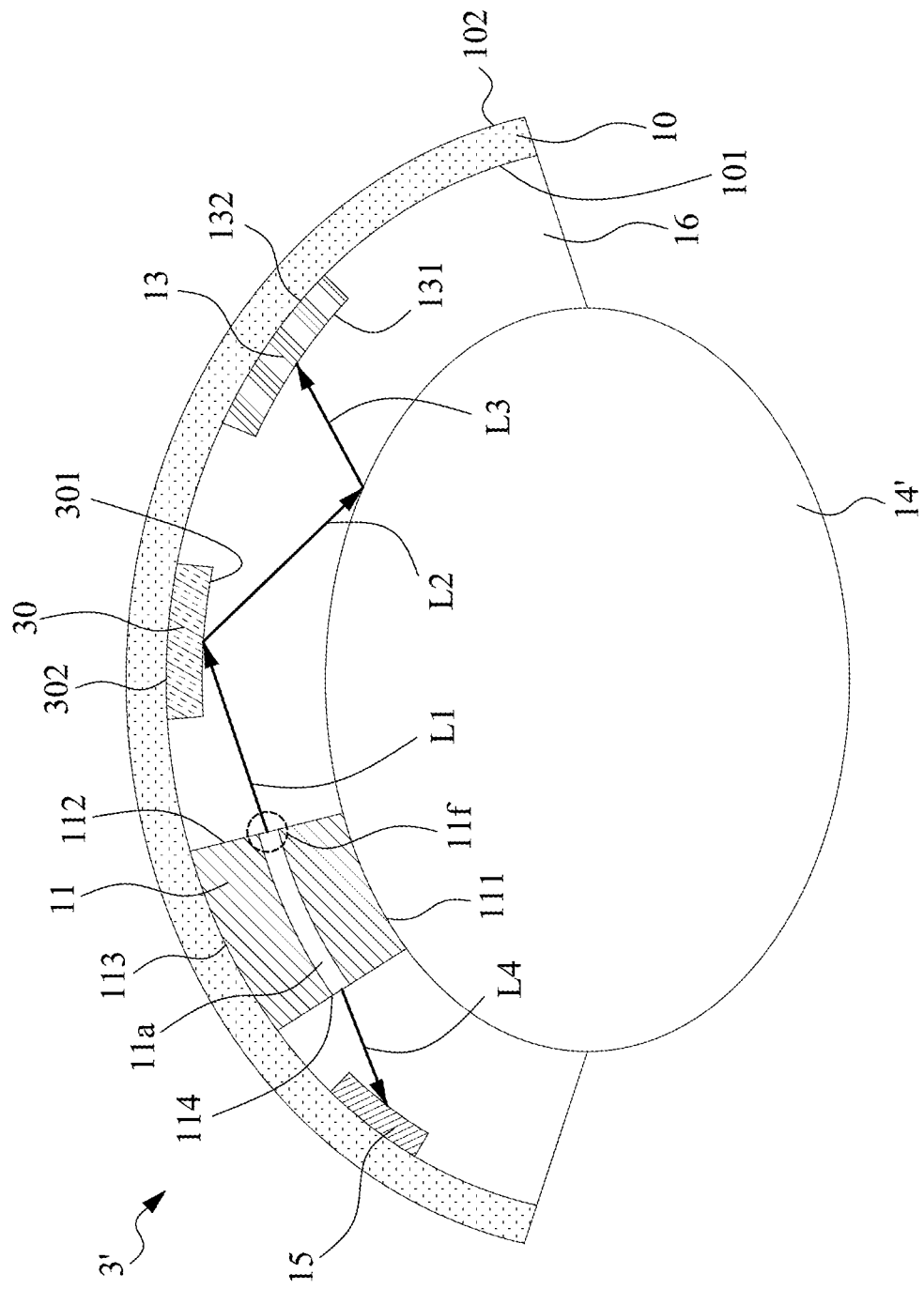
FIG. 3B is a cross-section of a sensing package and an object to be inspected in accordance with some arrangements of the present disclosure.

FIG. 3B is a cross-section of a sensing package 3' and the object 14' in accordance with some arrangements of the present disclosure. The sensing package 3' is similar to the sensing package 1' in FIG. 1B and the sensing package 3 in FIG. 3A except for the differences described as follows.

In some arrangements, the sensing package 3' may be conformal to the contour or the shape of a portion of the object 14' and may be curved. For example, when the sensing package 3' is worn on a wrist, the sensing package 3' may be conformal to the wrist and may be curved.

Similar to the sensing package 1' in FIG. 1B, the light path of the light L1, the light path of the light L2, the light path of the light L3 and the light path of the light L4 may be affected by the curvature of the sensing package 3'. For example, the functionality (or the sensing function, or the sensing process) of the sensing package 3' may be affected by the curvature thereof.

The sensing package 3' may further include the receiver 15 and the encapsulant 16, which are similar to the sensing package 1' in FIG. 1B.

Figure 4A:
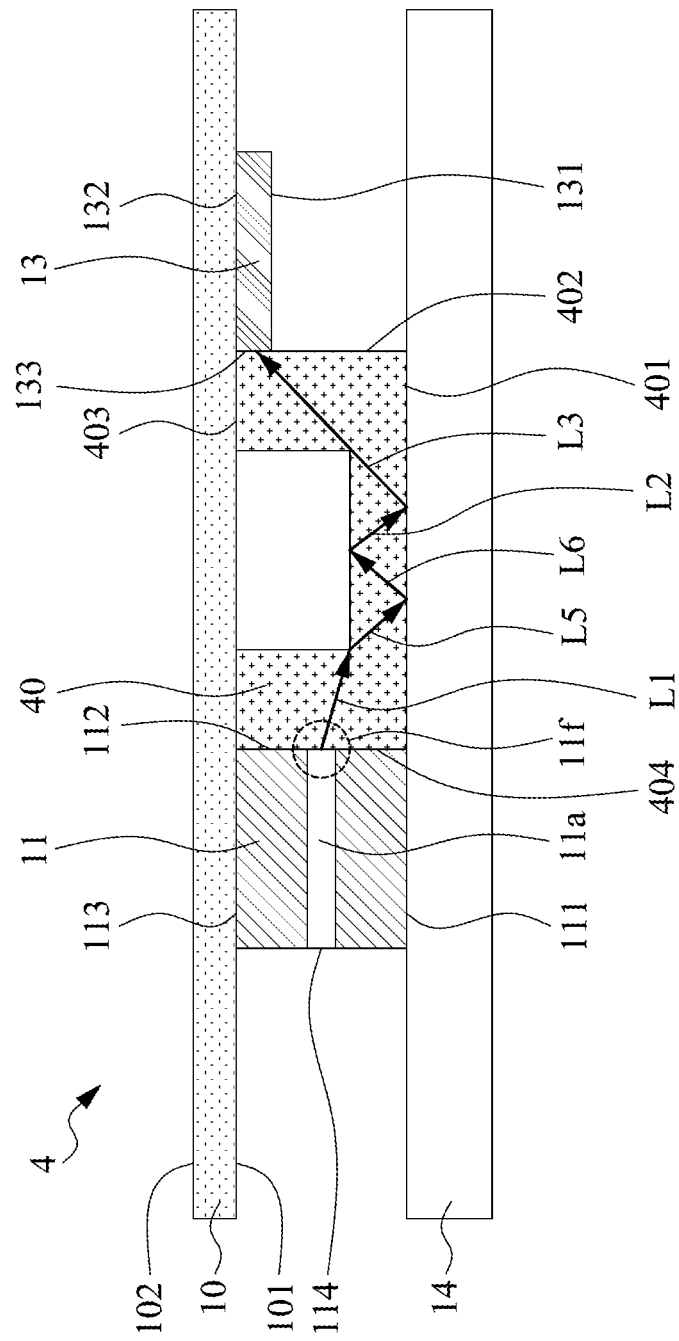
FIG. 4A is a cross-section of a sensing package and an object to be inspected in accordance with some arrangements of the present disclosure.

FIG. 4A is a cross-section of a sensing package 4 and the object 14 in accordance with some arrangements of the present disclosure. The sensing package 4 is similar to the sensing package 1 in FIG. 1A except for the differences described as follows.

The sensing package 4 may include a component 40. For example, the component 12 of the sensing package 1 may be replaced with the component 40 of the sensing package 4. The component 40 may be disposed between the emitter 11 and the receiver 13.

The component 40 may be configured to guide the light L1 from the emitter 11 toward the object 14, and then toward the receiver 13. As shown, the light L1 may enter the component 40, reflected by an internal surface (or a boundary) of the component 40 and become light L5 propagating toward the object 14. The light L5 may be reflected (e.g., by the object 14 or by an internal surface of the component 40) and become light L6 traveling back toward the internal surface of the component 40. Then, the light L6 may be reflected by the internal surface of the component 40 and become light L2 propagating toward the object 14. The light L2 may be reflected (e.g., by the object 14 or by an internal surface of the component 40) and become the light L3, which may be incident on the receiver 13.

In FIG. 4A, the propagating directions from the light L1 to the light L3 change four times. There may be five different propagating directions. In some other arrangements, the propagating directions from the light L1 to the light L3 may change more than four times, and there may be more than five different propagating directions. For example, there may be light L7, light L8 and light L9 (not illustrated in the figures) based on design requirements.

The component 40 may include any suitable shape or form to guide the light and change the propagating directions thereof. The component 40 may include an optical waveguide, such as optical fiber, a light pipe, etc. The component 40 may trap the light and total internal reflection may occur.

As shown, the component 40 may have a surface 401 facing or contacting the object 14 and a surface 403 facing or contacting the carrier 10. The component 40 may also have surfaces 402 and 404 extending between the surface 401 and the surface 403. The component 40 may have an internal surface (or a boundary) opposite to the surface 401. In some arrangements, the internal surface may define an empty space or an air cavity.

The surface 404 may be configured to receive the light L1. The surface 404 may contact the surface 112 of the emitter 11. The surface 404 may contact the end facet 11f (or front facet, or a light-emitting surface or region) on the surface 112 of the emitter 11.

The surface 402 may be configured to output the light L3. The surface 402 may contact a surface (such as a lateral surface extending between the surface 131 and the surface 132) of the receiver 13. In some arrangements, an active surface (e.g., the lateral surface or the surface 131) may be configured to receive the light L3. For example, the light L3 may be incident on the lateral surface, as shown in FIG. 4A. However, in some other arrangements, the light L3 may be incident on the surface 131.

Figure 4B:
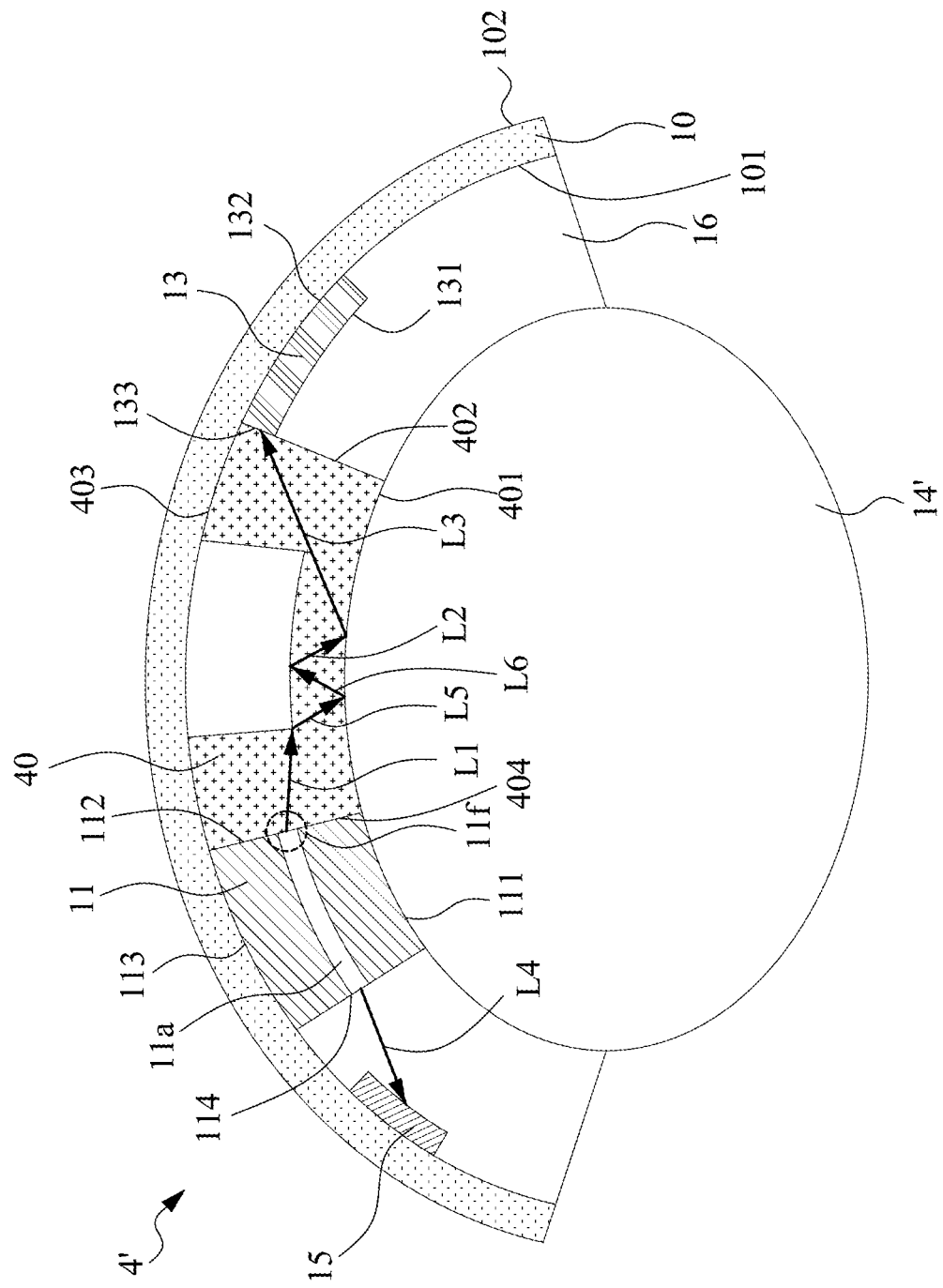
FIG. 4B is a cross-section of a sensing package and an object to be inspected in accordance with some arrangements of the present disclosure.

FIG. 4B is a cross-section of a sensing package 4' and the object 14' in accordance with some arrangements of the present disclosure. The sensing package 4' is similar to the sensing package 1' in FIG. 1B and the sensing package 4 in FIG. 4A except for the differences described as follows.

In some arrangements, the sensing package 4' may be conformal to the contour or the shape of a portion of the object 14' and may be curved. For example, when the sensing package 4' is worn on a wrist, the sensing package 4' may be conformal to the wrist and may be curved.

Similar to the sensing package 1' in FIG. 1B, the light path of the light L1, the light path of the light L2, the light path of the light L3, the light path of the light L4, the light path of the light L5 and the light path of the light L6 may be affected by the curvature of the sensing package 4'. For example, the functionality (or the sensing function, or the sensing process) of the sensing package 4' may be affected by the curvature thereof.

The sensing package 4' may further include the receiver 15 and the encapsulant 16, which are similar to the sensing package 1' in FIG. 1B.

Figure 4C:
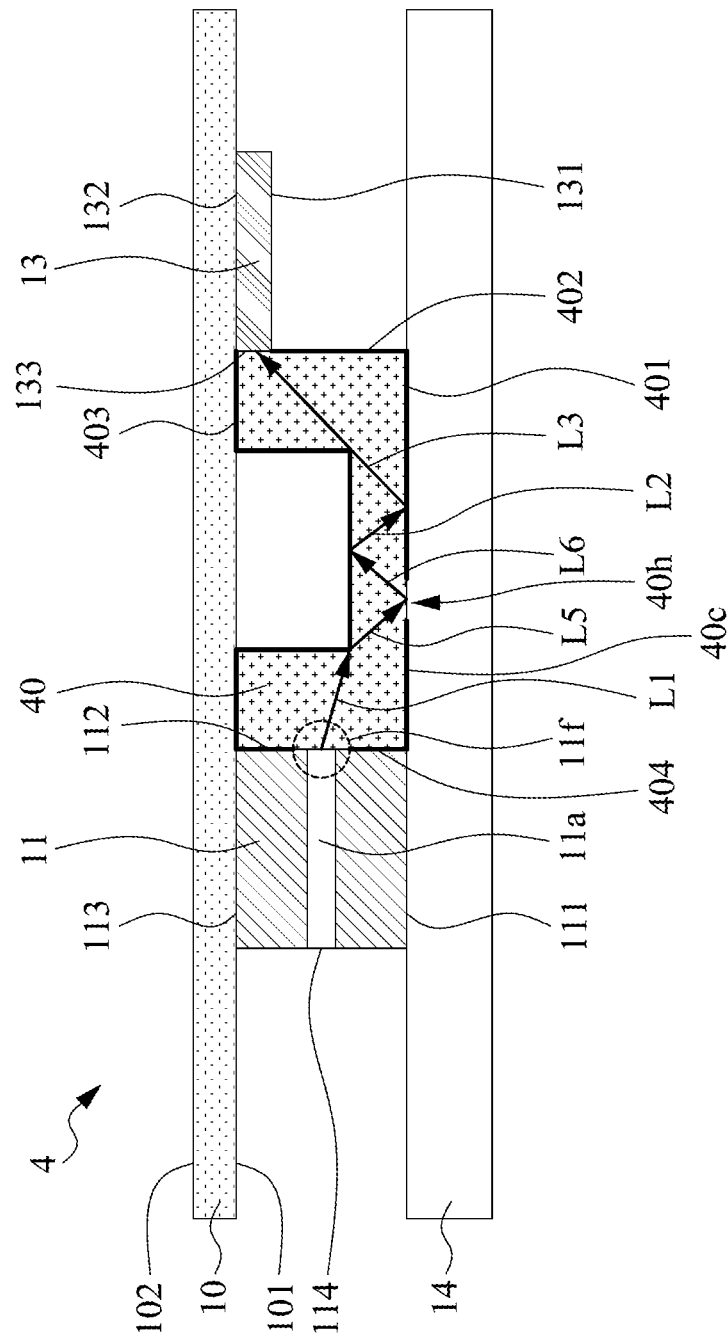
FIG. 4C is a cross-section of a sensing package and an object to be inspected in accordance with some arrangements of the present disclosure.

FIG. 4C is a cross-section of a sensing package and the object 14 in accordance with some arrangements of the present disclosure. The sensing package in FIG. 4C is similar to the sensing package 4 in FIG. 4A except that the component 40 of the sensing package in FIG. 4C further includes a cladding layer 40c. The cladding layer 40c may contact the object 14. In some embodiments, the cladding layer 40c may define an opening 40h. The opening 40h may be exposed to the object 14.

In some embodiments, the light L1 may enter the component 40, reflected by an internal surface (or a boundary) of the component 40 and become light L5, which may be incident on the object 14 through the opening 40h. The light L5 may be reflected by the object 14 and become light L6 traveling back toward the internal surface of the component 40. Then, the light L6 may be reflected by the internal surface of the component 40 and become light L2 propagating toward the object 14. The light L2 may be reflected and become the light L3, which may be incident on the receiver 13.

Figure 4D:
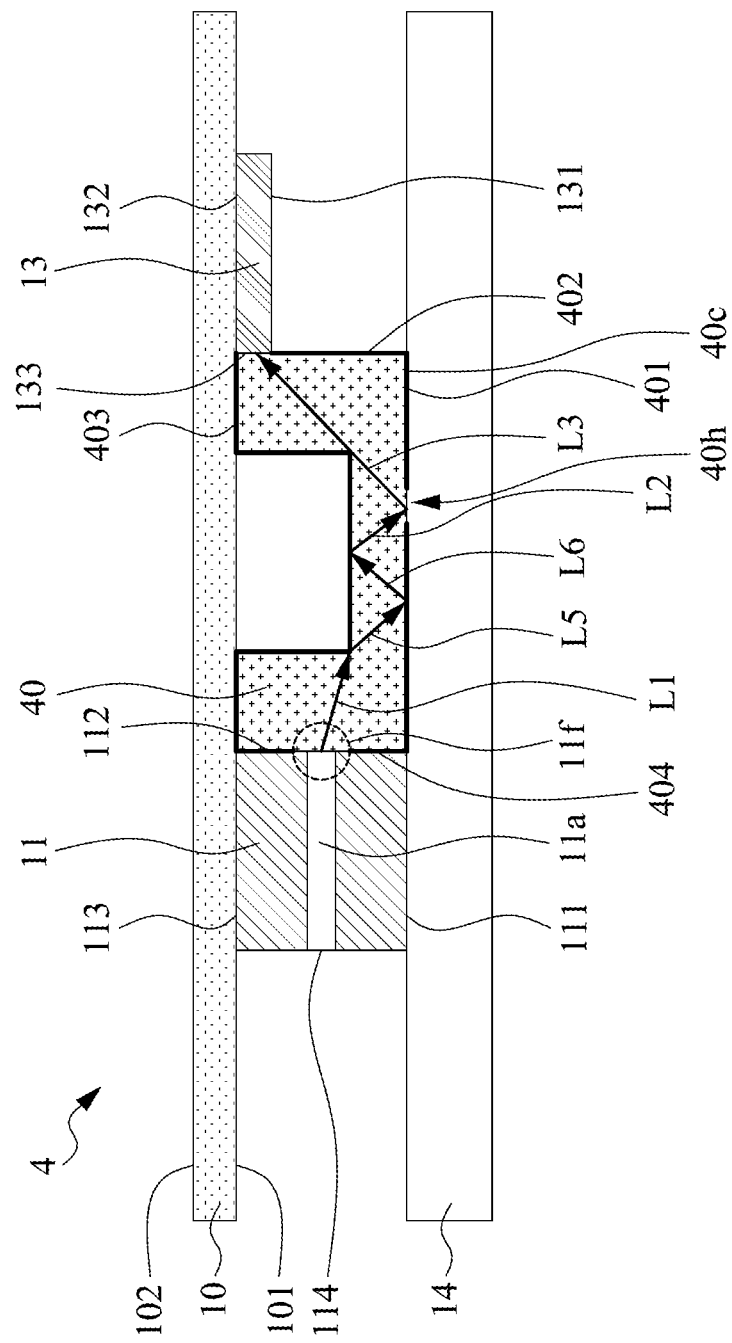
FIG. 4D is a cross-section of a sensing package and an object to be inspected in accordance with some arrangements of the present disclosure.

FIG. 4D is a cross-section of a sensing package and the object 14 in accordance with some arrangements of the present disclosure. The sensing package in FIG. 4D is similar to the sensing package in FIG. 4D except for the different location of the opening 40h.

In some embodiments, the light L1 may enter the component 40, reflected by an internal surface (or a boundary) of the component 40 and become light L5 propagating toward the object 14. The light L5 may be reflected and become light L6 traveling back toward the internal surface of the component 40. Then, the light L6 may be reflected by the internal surface of the component 40 and become light L2, which may be incident on the object 14 through the opening 40h. The light L2 may be reflected by the object 14 and become the light L3, which may be incident on the receiver 13.

Figure 5A:
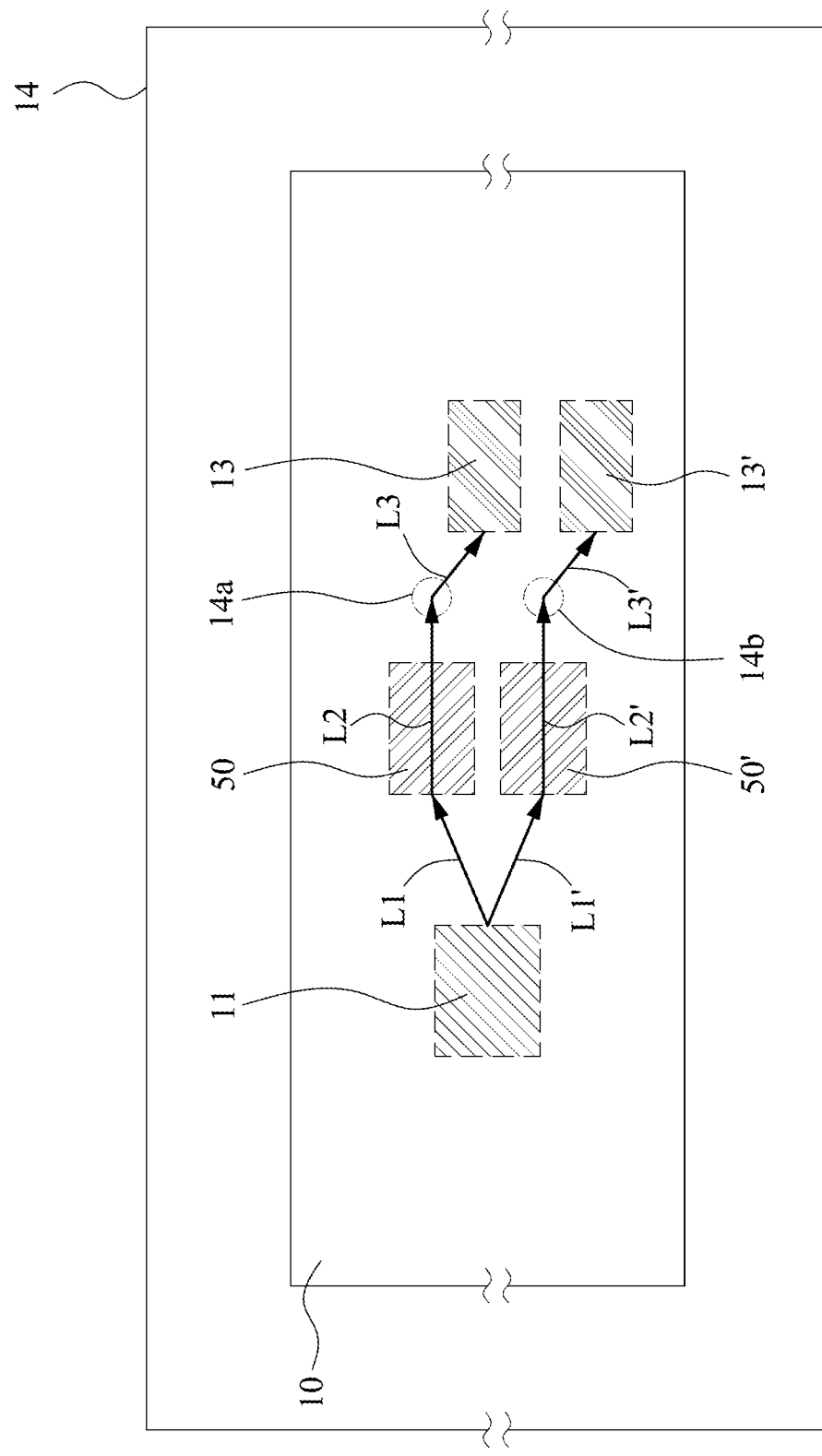
FIG. 5A is a top view of a sensing package in accordance with some arrangements of the present disclosure.

FIG. 5A is a top view of a sensing package 5 in accordance with some arrangements of the present disclosure. The sensing package 5 is similar to the sensing package 1 in FIG. 1A except for the differences described as follows.

The sensing package 5 may include two components 50, 50' and two receivers 13, 13'.

The emitter 11 may be configured to generate or emit light L1 toward the component 50 and to generate or emit light L1' toward the component 50'. The light L1 and the light L1' may be of a single wavelength or a single frequency. The light L1 and the light L1' may have different propagating directions.

The components 50 and 50' may be similar to the optical devices or optics (such as the components 12, 20, 30 and 40) described.

For example, the component 50 may be configured to change the light L1 into light L2 having a propagating direction different from that of the light L1. For example, the component 50 may be configured to direct the light L1 toward a region 14a of an object (such as the object 14 in FIG. 1A). The light L2 may be reflected by the region 14a of the object as light L3, which may be incident on the receiver 13.

For example, the component 50' may be configured to change the light L1' into light L2' having a propagating direction different from that of the light L1'. For example, the component 50' may be configured to direct the light L1' toward a region 14b of the object (such as the object 14 in FIG. 1A). The region 14b may be distinct from the region 14a. The light L2' may be reflected by the region 14b of the object as light L3', which may be incident on the receiver 13'.

As shown in FIG. 5A, the sensing package 5 includes separated components for receiving the light L3 and the light L3'. However, the present disclosure is not limited thereto. In some other embodiments, the sensing package 5 may include a single or a unitary receiver having two light-receiving regions configured to receive the light L3 and the light L3'.

The positions, functions, and number of the components (such as the components 50 and 50') and the receivers (such as the receivers 13 and 13') in the sensing package 5 are not intended to limit the present disclosure. For example, there may be any number of components and receivers in the sensing package 5 due to design requirements.

Figure 5B:
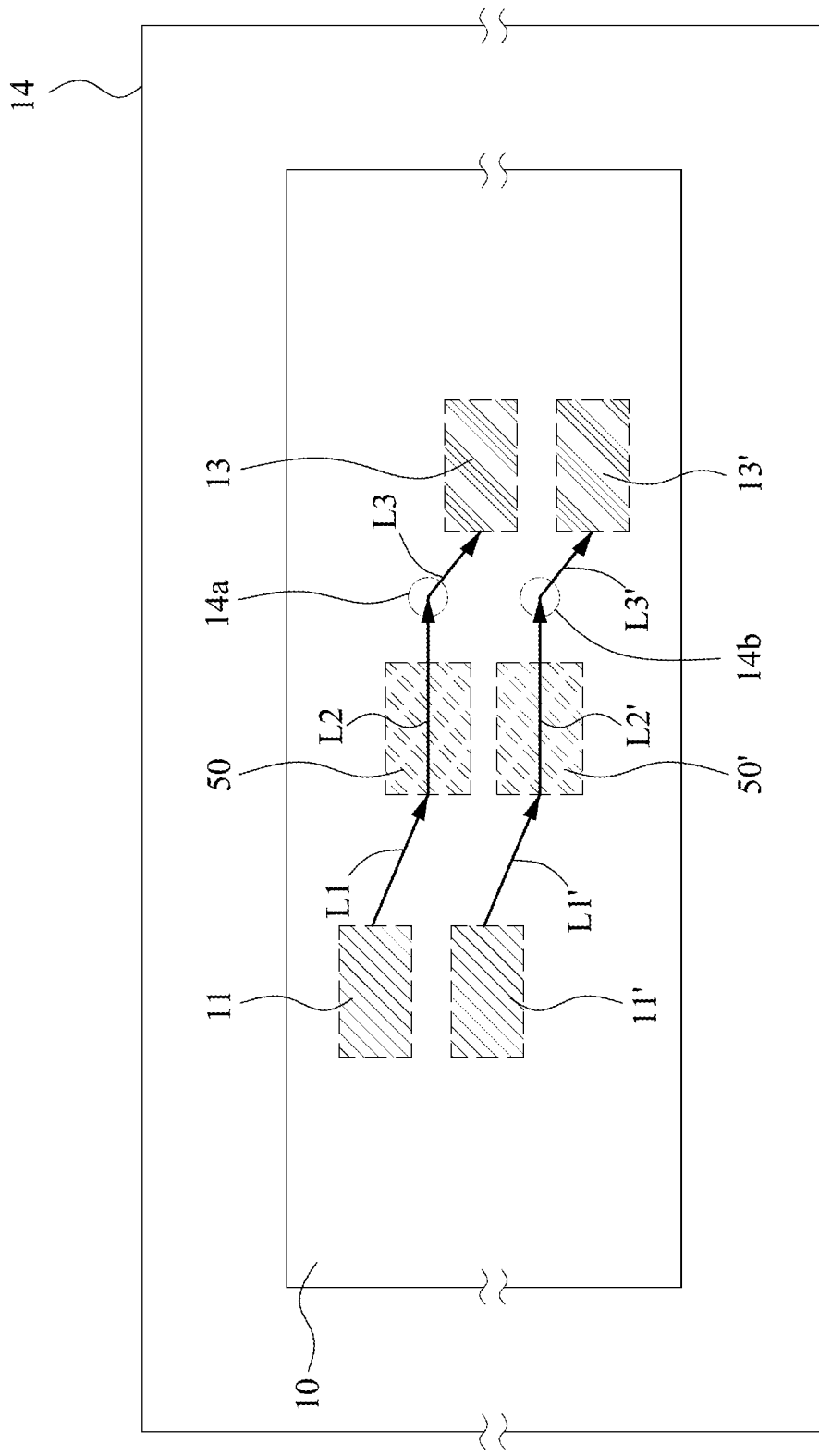
FIG. 5B is a top view of a sensing package in accordance with some arrangements of the present disclosure.

FIG. 5B is a top view of a sensing package 5' in accordance with some arrangements of the present disclosure. The sensing package 5' is similar to the sensing package 5 in FIG. 5A except for the differences described as follows.

The sensing package 5' may include two emitters 11, 11', two components 50, 50' and two receivers 13, 13'.

The emitter 11 may be configured to generate or emit light L1 toward the component 50. The emitter 11' may be configured to generate or emit light L1' toward the component 50'. The light L1 and the light L1' may be of different wavelengths or different frequencies. The light L1 and the light L1' may have different propagating directions.

As shown in FIG. 5B, the sensing package 5' includes separated components (such as separated transmitters (TXs)) for emitting the light L1 and the light L1'. However, the present disclosure is not limited thereto. In some other embodiments, the sensing package 6 may include a single or a unitary emitter having two light-emitting regions configured to emitting the light L1 and the light L1'.

The components 50 and 50' may be similar to the optical devices or optics (such as the components 12, 20, 30, 40) described.

The receivers 13 and 13' may be configured to receive light of different wavelengths or different frequencies.

Figure 6A:
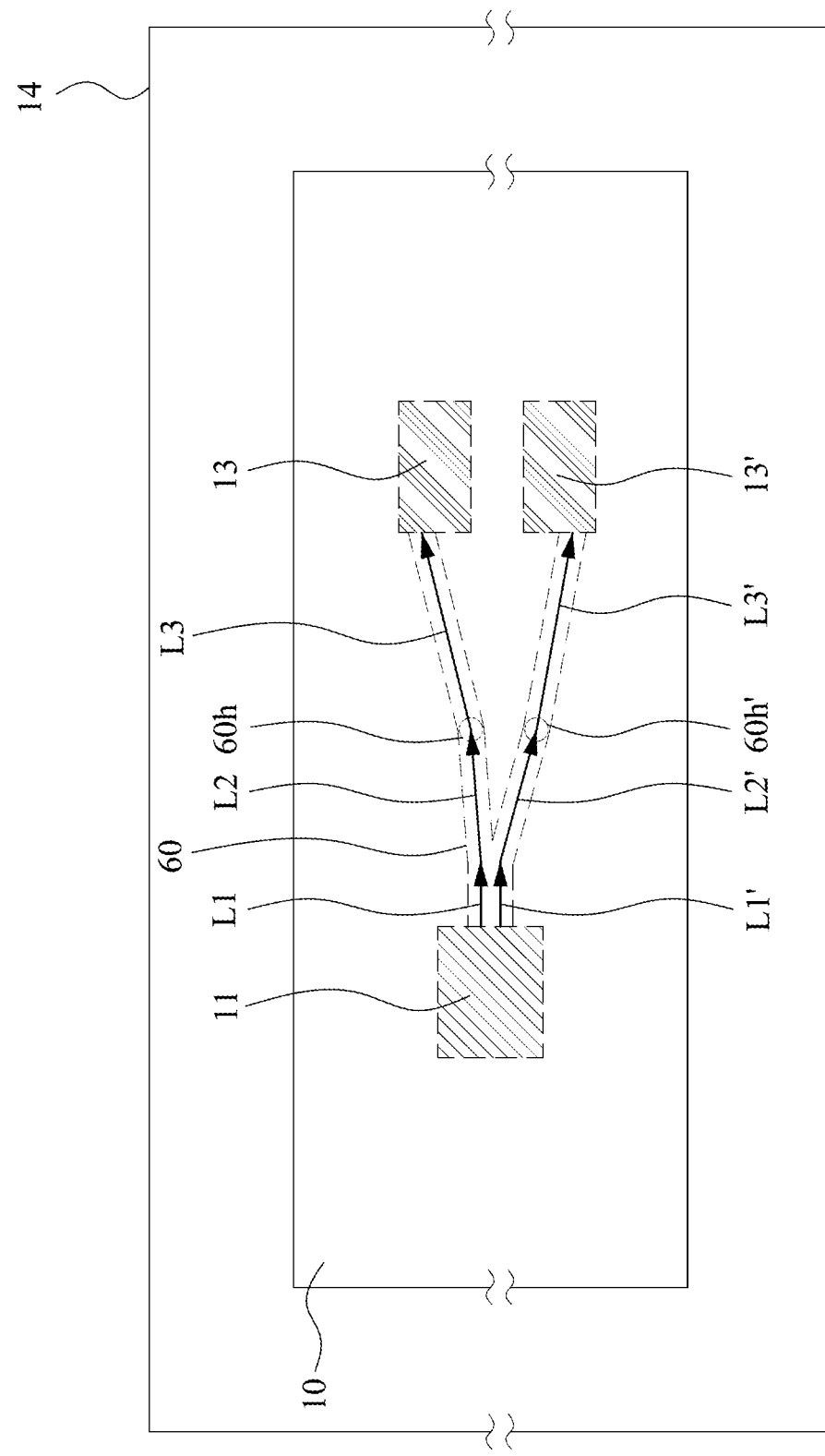
FIG. 6A is a top view of a sensing package in accordance with some arrangements of the present disclosure.

FIG. 6A is a top view of a sensing package 6 in accordance with some arrangements of the present disclosure. The sensing package 6 is similar to the sensing package 1 in FIG. 1A except for the differences described as follows.

The sensing package 6 may include a component 60 and two receivers 13, 13'. The component 60 may be similar to the component 40 in FIG. 4A. For example, the component 60 may include an optical waveguide, such as optical fiber, a light pipe, etc. The component 60 may trap the light and total internal reflection may occur. In some embodiments, the component 60 may have one end connecting to the emitter 11 and two ends connecting to the receivers 13 and 13'. For example, the component 60 branches off to the receivers 13 and 13'.

In some embodiments, the component 60 may directly contact the emitter 11 and/or the receivers 13 and 13'. In some other embodiments, the component 60 may be spaced apart from the emitter 11 and/or the receivers 13 and 13'. For example, a gap may be defined or exist between an end of the component 60 and the emitter 11. For example, a gap may be defined or exist between an end of the receiver 13 and the emitter 11. For example, a gap may be defined or exist between an end of the receiver 13' and the emitter 11.

The emitter 11 may be configured to generate or emit light L1 and the light L1'. The light L1 and the light L1' may be of a single wavelength or a single frequency. The light L1 and the light L1' may have different propagating directions. The light L1 and the light L1' may propagate through different branches of the component 60.

The component 60 may have openings 60h and 60h' exposed to the object 14. In some embodiments, the light L1 may enter the component 60, reflected by an internal surface (or a boundary) of the component 60 and become light L2, which may be incident on the object 14 through the opening 60h. The light L2 may be reflected by the object 14 and become the light L3, which may be incident on the receiver 13. Similarly, the light L1' may enter the component 60, reflected by an internal surface (or a boundary) of the component 60 and become light L2', which may be incident on the object 14 through the opening 60h'. The light L2' may be reflected by the object 14 and become the light L3', which may be incident on the receiver 13'.

Figure 6B:
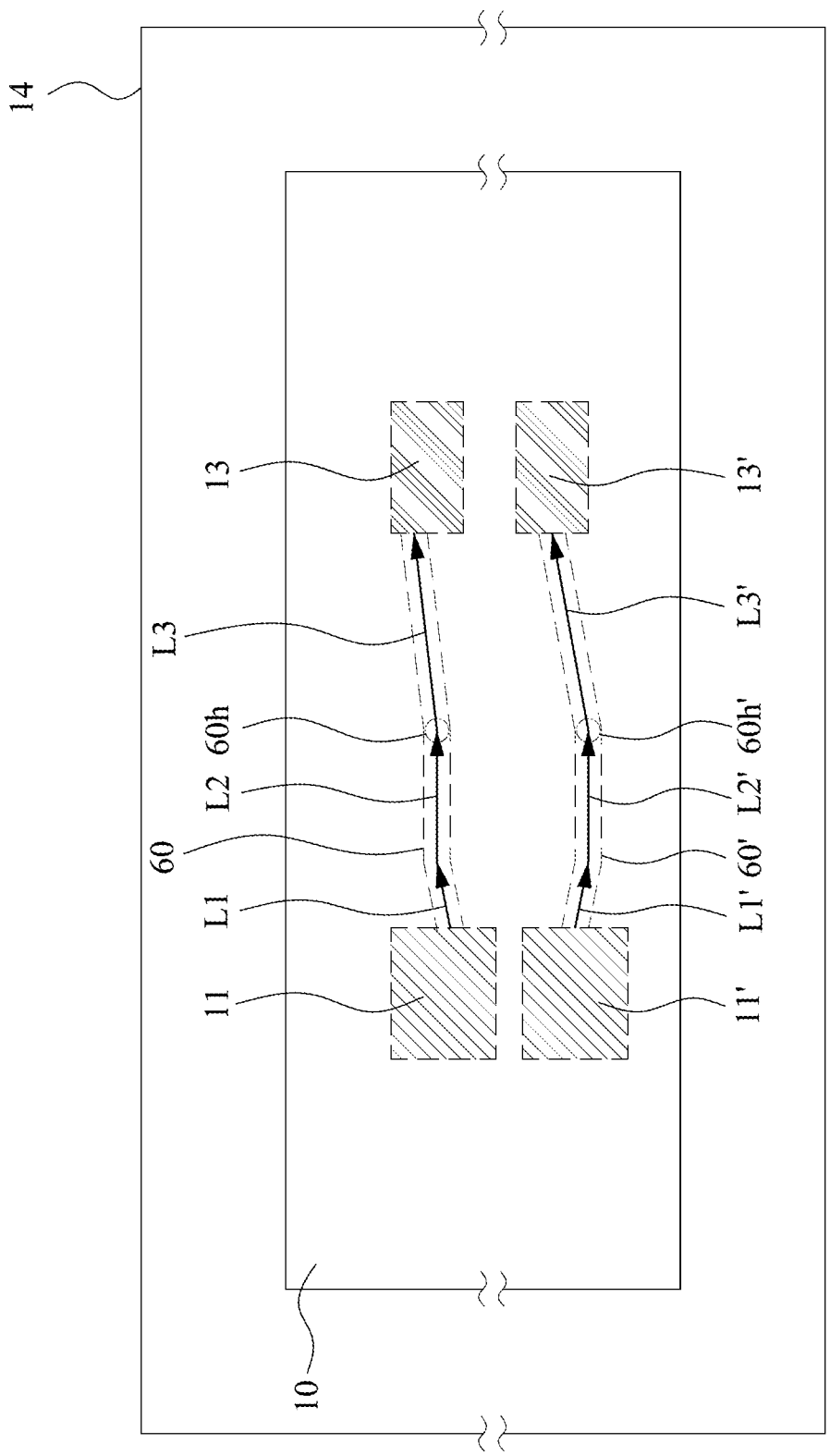
FIG. 6B is a top view of a sensing package in accordance with some arrangements of the present disclosure.

FIG. 6B is a top view of a sensing package 6' in accordance with some arrangements of the present disclosure. The sensing package 6' is similar to the sensing package 6 in FIG. 6A except for the differences described as follows.

The sensing package 6' may include two emitters 11, 11', the component 60 and two receivers 13, 13'.

The emitter 11 may be configured to generate or emit light L1. The emitter 11' may be configured to generate or emit light L1'. The light L1 and the light L1' may be of different wavelengths or different frequencies. The light L1 and the light L1' may have different propagating directions.

In some embodiments, the component 60 may directly contact the emitter 11 and/or the emitter 11'. In some other embodiments, the component 60 may be spaced apart from the emitter 11 and/or the emitter 11'. For example, a gap may be defined or exist between an end of the component 60 and the emitter 11. For example, a gap may be defined or exist between an end of the component 60 and the emitter 11'.

According to some arrangements of the present disclosure, the propagating directions of light in the sensing package may be changed through optical principles, such as using optical prism, a lens, an optical waveguide, a reflecting surface, or other optical devices or optics as described.

In some other arrangements, the propagating directions of light in the sensing package may be changed through non-optical principles, such as through ways without using optical devices or optics to change the propagating directions. For example, the propagating directions of light may be changed through adjusting a density of a medium in which the light are propagating. For example, the density of the medium may be adjusted by changing a temperature of the medium. For example, the propagating directions of light may be changed through applying an electric field, a magnetic field, or an electromagnetic field on the light.

As used herein, the singular terms "a," "an," and "the" may include a plurality of referents unless the context clearly dictates otherwise.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to #1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" parallel can refer to a range of angular variation relative to 0° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, "substantially" perpendicular can refer to a range of angular variation relative to 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific arrangements thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other arrangements of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. An optical module, comprising:
a carrier configured to face an object to be inspected;
an emitter device disposed adjacent to the carrier and configured to emit a first light;
a receiver device disposed between the carrier and the object; and
an optical device configured to direct the first light toward the object;
wherein the receiver device is configured to receive a second light reflected by the object, wherein the optical device is configured to direct the first light into a first region of the object and into a second region distinct from the first region.

2. The optical module of claim 1, wherein the receiver device comprises a first receive component configured to receive the second light reflected from the first region.

3. The optical module of claim 2, wherein the receiver device comprises a second receive component configured to receive a third light reflected from the second region.

4. An optical module, comprising:
a carrier configured to face an object to be inspected;
an emitter device disposed adjacent to the carrier and configured to emit a first light;
a receiver device disposed between the carrier and the object; and
an optical device configured to direct the first light toward the object;
wherein the receiver device is configured to receive a second light reflected by the object, wherein the emitter device is configured to emit a fourth light, and the optical device directs the first light and the fourth light to different regions of the object.

5. The optical module of claim 4, wherein the emitter device comprises a first transmitter configured to emit the first light and a second transmitter configured to emit the fourth light.

6. An optical module, comprising:
a carrier configured to face an object to be inspected;
an emitter device disposed adjacent to the carrier and configured to emit a first light;
a receiver device disposed between the carrier and the object; and
an optical device configured to direct the first light toward the object;
wherein the receiver device is configured to receive a second light reflected by the object, wherein the optical device is configured to receive the first light propagating in a first direction and to output a fifth light propagating in a second direction, and wherein the receiver device is configured to receive the second light reflected into a third direction.

7. The optical module of claim 6, wherein a sixth light presents in a light path between the first light and the fifth light.

8. The optical module of claim 6, wherein the second light is reflected from the fifth light by the object.

* * * * *